(12) United States Patent
Herzog et al.

(10) Patent No.: US 10,557,552 B2
(45) Date of Patent: Feb. 11, 2020

(54) TROUGH SEAL

(71) Applicant: Cardiac Pacemakers, Inc., St. Paul, MN (US)

(72) Inventors: Phil Herzog, Shoreview, MN (US); Brian Finander, Vadnais Heights, MN (US); Luis Bruno, Zarcero (CR); Justin Strike, Hanover, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 88 days.

(21) Appl. No.: 15/818,737

(22) Filed: Nov. 20, 2017

(65) Prior Publication Data
US 2018/0142787 A1 May 24, 2018

Related U.S. Application Data (60) Provisional application No. 62/425,001, filed on Nov. 21, 2016.

(51) Int. Cl.
*F16J 15/02* (2006.01)
*A61M 39/06* (2006.01)
*A61M 25/06* (2006.01)
*A61N 1/05* (2006.01)

(52) U.S. Cl.
CPC ........ *F16J 15/022* (2013.01); *A61M 25/0662* (2013.01); *A61M 39/0613* (2013.01); *A61N 1/056* (2013.01); *A61M 2039/064* (2013.01); *A61M 2205/0216* (2013.01)

(58) Field of Classification Search
CPC .............. F16J 15/022; A61M 25/0662; A61M 39/0613; A61M 2039/064; A61M 2205/0216
See application file for complete search history.

(56) References Cited

U.S. PATENT DOCUMENTS

| | | |
|---|---|---|
| 3,113,586 A | 12/1963 | Edmark, Jr. |
| 4,634,432 A | 1/1987 | Kocak |
| 4,655,752 A | 4/1987 | Honkanen et al. |
| 4,747,840 A | 5/1988 | Ladika et al. |
| 4,798,594 A | 1/1989 | Hillstead |
| 4,895,346 A | 1/1990 | Steigerwald |
| 4,895,565 A | 1/1990 | Hillstead |
| 4,909,798 A | 3/1990 | Fleischhacker et al. |
| 4,917,668 A | 4/1990 | Haindl |

(Continued)

FOREIGN PATENT DOCUMENTS

| | | |
|---|---|---|
| EP | 2213327 A1 | 8/2010 |
| JP | 10500345 A | 1/1998 |

(Continued)

OTHER PUBLICATIONS

International Preliminary Report on Patentability issued in PCT/US2014/068673, dated Jun. 16, 2016, 8 pages.

(Continued)

*Primary Examiner* — Eugene G Byrd
(74) *Attorney, Agent, or Firm* — Faegre Baker Daniels LLP (57) ABSTRACT

A seal to permit the passage of a device through the seal. The seal includes an elastic component having a proximal end, a distal end, and an elongated trough adjacent the distal end. The elastic component has a slit that intersects the elongated trough.

17 Claims, 7 Drawing Sheets

(56) References Cited

U.S. PATENT DOCUMENTS

| | | | |
|---|---|---|---|
| 4,929,235 A | 5/1990 | Merry et al. | |
| 5,000,745 A | 3/1991 | Guest et al. | |
| 5,114,408 A | 5/1992 | Fleischhaker et al. | |
| 5,125,903 A | 6/1992 | McLaughlin et al. | |
| 5,149,327 A | 9/1992 | Oshiyama | |
| 5,167,637 A | 12/1992 | Okada et al. | |
| 5,324,271 A | 6/1994 | Abiuso et al. | |
| 5,330,437 A | 7/1994 | Durman | |
| 5,385,552 A | 1/1995 | Haber et al. | |
| 5,520,655 A | 5/1996 | Davila et al. | |
| 5,549,576 A * | 8/1996 | Patterson | A61M 25/0662 251/149.1 |
| 5,591,137 A | 1/1997 | Stevens | |
| 5,613,956 A * | 3/1997 | Patterson | A61M 25/0662 604/167.04 |
| 5,643,227 A | 7/1997 | Stevens | |
| 5,693,025 A | 12/1997 | Stevens | |
| 5,743,884 A | 4/1998 | Hasson et al. | |
| 5,827,227 A * | 10/1998 | DeLago | A61M 25/0662 604/104 |
| 5,882,345 A * | 3/1999 | Yoon | A61B 17/3439 604/104 |
| 5,935,112 A | 8/1999 | Stevens et al. | |
| 6,024,729 A | 2/2000 | Dehdashtian et al. | |
| 6,083,207 A | 7/2000 | Heck | |
| 6,086,570 A | 7/2000 | Aboul-Hosn et al. | |
| 6,142,981 A | 11/2000 | Heck et al. | |
| 6,238,373 B1 | 5/2001 | de la Torre et al. | |
| 6,331,176 B1 | 12/2001 | Becker et al. | |
| 6,352,520 B1 * | 3/2002 | Miyazaki | A61M 39/045 604/167.03 |
| 6,551,283 B1 | 4/2003 | Guo et al. | |
| 6,602,240 B2 | 8/2003 | Hermann et al. | |
| 6,623,460 B1 | 9/2003 | Heck | |
| 6,632,200 B2 | 10/2003 | Guo et al. | |
| 6,634,364 B2 | 10/2003 | Westlund et al. | |
| 6,702,255 B2 | 3/2004 | Dehdashtian | |
| 6,702,828 B2 | 3/2004 | Whayne | |
| 6,723,073 B2 | 4/2004 | Ley et al. | |
| 7,081,106 B1 | 7/2006 | Guo et al. | |
| 7,101,353 B2 | 9/2006 | Lui et al. | |
| 7,192,433 B2 | 3/2007 | Osypka et al. | |
| 7,226,433 B2 | 6/2007 | Bonnette et al. | |
| 7,241,276 B2 | 7/2007 | Argentine et al. | |
| 7,497,844 B2 | 3/2009 | Spear et al. | |
| 7,731,694 B2 | 6/2010 | Becker et al. | |
| 7,967,790 B2 | 6/2011 | Whiting et al. | |
| 7,985,232 B2 | 7/2011 | Potter et al. | |
| 8,048,033 B2 | 11/2011 | Becker et al. | |
| 8,137,317 B2 | 3/2012 | Osypka | |
| 8,142,446 B2 | 3/2012 | Shan | |
| 8,262,671 B2 | 9/2012 | Osypka | |
| 8,273,059 B2 | 9/2012 | Nardeo et al. | |
| 8,382,715 B2 | 2/2013 | Nardeo et al. | |
| 8,486,024 B2 | 7/2013 | Steube | |
| 8,512,293 B2 | 8/2013 | Leeflang et al. | |
| 8,523,822 B2 | 9/2013 | Nardeo et al. | |
| 8,905,973 B2 | 12/2014 | Tegg et al. | |
| 2002/0010425 A1 | 1/2002 | Guo et al. | |
| 2002/0072712 A1 | 6/2002 | Nool et al. | |
| 2002/0077683 A1 | 6/2002 | Westlund et al. | |
| 2003/0085373 A1 | 5/2003 | Dehdashtian | |
| 2004/0049158 A1 | 3/2004 | Ley et al. | |
| 2004/0210194 A1 | 10/2004 | Bonnette et al. | |
| 2004/0260243 A1 | 12/2004 | Rickerd | |
| 2004/0267202 A1 | 12/2004 | Potter | |
| 2005/0020981 A1 | 1/2005 | Kurth | |
| 2005/0033239 A1 | 2/2005 | Argentine | |
| 2005/0192537 A1 | 9/2005 | Osborne et al. | |
| 2005/0228346 A1 | 10/2005 | Goode et al. | |
| 2006/0030825 A1 | 2/2006 | Enns et al. | |
| 2006/0135972 A1 | 6/2006 | Zeiner | |
| 2006/0135977 A1 | 6/2006 | Thompson et al. | |
| 2009/0209914 A1 * | 8/2009 | Koch | A61M 39/0613 604/167.02 |
| 2010/0094225 A1 | 4/2010 | Hastings et al. | |
| 2010/0094228 A1 * | 4/2010 | Bettuchi | A61B 17/3421 604/167.03 |
| 2010/0292646 A1 * | 11/2010 | Nardeo | A61M 25/0662 604/164.05 |
| 2010/0312190 A1 | 12/2010 | Searfoss et al. | |
| 2012/0065612 A1 | 3/2012 | Stout et al. | |
| 2012/0221024 A1 | 8/2012 | Sutton et al. | |
| 2012/0245527 A1 | 9/2012 | Stephens et al. | |
| 2013/0310765 A1 | 11/2013 | Stephens et al. | |
| 2015/0157843 A1 | 6/2015 | Pepin et al. | |
| 2016/0331935 A1 * | 11/2016 | Saatchi | A61M 25/0606 |
| 2017/0080200 A1 * | 3/2017 | Bickhart | A61M 39/0606 |
| 2017/0326341 A1 * | 11/2017 | Liska | A61M 25/0606 |
| 2018/0169396 A1 * | 6/2018 | Olson | A61B 17/3423 |

FOREIGN PATENT DOCUMENTS

| | | |
|---|---|---|
| JP | 2008529672 A | 8/2008 |
| JP | 2010508905 A | 3/2010 |
| WO | WO9906099 A2 | 2/1999 |
| WO | 2009041522 A1 | 4/2009 |
| WO | 2015085123 A1 | 6/2015 |

OTHER PUBLICATIONS

International Search Report and Written Opinion issued in PCT/US2014/068673, dated Apr. 22, 2015, 11 pages.

International Search Report and Written Opinion issued in PCT/US2017/062654, dated Feb. 26, 2018, 12 pages.

International Search Report and Written Opinion of International Application No. PCT/US2006/060159, filed Oct. 23, 2006, dated Jun. 18, 2007.

* cited by examiner

TROUGH SEAL

CROSS-REFERENCE TO RELATED APPLICATION

This application claims priority to Provisional Application No. 62/425,001, filed Nov. 21, 2016, which is herein incorporated by reference in its entirety.

TECHNICAL FIELD

The present disclosure relates to fluid seals. More specifically, the disclosure relates to medical devices and methods for providing a seal around a device inserted through the seal to reduce or prevent leakage of fluids through the seal and past the device.

BACKGROUND

Some seals are intended to conform to the contours of devices inserted through the seals to reduce or prevent leakage of fluids through the seals and past the devices. These seals may be used in a variety of fields including the automotive, manufacturing equipment, and medical fields.

In the medical field, in various medical procedures one or more medical instruments may be inserted into the arteries or veins of a patient and advanced to a location requiring treatment or diagnosis. For example, a catheter may be advanced through the patient's vasculature to a desired location, such as the heart, for delivery of a lead, such as a cardiac lead. A medical instrument including the catheter can include a seal located at the proximal end of the catheter to inhibit the flow of blood out of the catheter lumen. A catheter lead or other device can be inserted through the seal and the catheter lumen to the location requiring treatment or diagnosis. The seal inhibits fluid flow through the seal and past the catheter lead.

Some flexible seals are intended to conform around devices inserted through a slit cut through the seal. These seals retard the flow of fluid, including blood and air, through the seal and past the device. However, sometimes, a passage on one or more sides of the device inserted through the slit in the seal remains separated, such that fluid may flow through the separated passage. Excess blood may leak through the seal when the catheter rests in the vasculature and air may leak through the seal and into the catheter when the catheter is aspirated. This may force the physician to abort the lead placement procedure and dispose of the catheter and the lead, which increases procedure time and cost.

SUMMARY

Example 1 is a seal configured to permit passage of a device through the seal. The seal includes an elastic component having a proximal end, a distal end, and an elongated trough adjacent the distal end, the elastic component having a slit that intersects the elongated trough.

Example 2 is the seal of Example 1, wherein the elastic component has an elongated inner cavity having a cavity depth extending between the proximal end and the distal end of the elastic component, the elongated inner cavity having a cavity length and a cavity width that is shorter than the cavity length and the elongated trough having a trough length and a trough width that is shorter than the trough length, wherein the trough length is parallel to the cavity length.

Example 3 is the seal of any one of Examples 1 and 2, wherein the slit intersects the elongated trough at an oblique angle.

Example 4 is the seal of any one of Examples 1 and 2, wherein the slit intersects the elongated trough perpendicular to the elongated trough.

Example 5 is the seal of any one of Examples 1-4, wherein the elastic component includes one or more flaps of elastic material at the distal end and bottom of the elongated trough, the one or more flaps configured for forming a fluid seal around the device inserted through the seal.

Example 6 is the seal of Example 5, wherein the one or more flaps have a thickness in a range from 0.005 to 0.01 inches thick.

Example 7 is the seal of any one of Examples 1-6, wherein the elastic component has an opening at the proximal end for inserting the device through the elongated trough.

Example 8 is the seal of any one of Examples 1-7, wherein a top profile of the elastic component is substantially one of circular, oblong, rectangular, and polygon shaped.

Example 9 is a seal configured to permit passage of a medical device through the seal. The seal includes an elastic component having a proximal end, a distal end, and an elongated inner cavity between the proximal end and the distal end, the elongated inner cavity having an elongated trough that is adjacent the distal end of the elastic component, wherein the elastic component has a slit that intersects the elongated trough.

Example 10 is the seal of Example 9, wherein the elastic component includes one or more flaps of elastic material at the distal end and bottom of the elongated trough, the one or more flaps configured to form a fluid seal around the medical device to reduce leakage of blood and air through the seal.

Example 11 is the seal of any one of Examples 9 and 10, wherein the elastic component is configured to be cut along at least one side of the slit to remove the seal from the medical device.

Example 12 is the seal of any one of Examples 9-11, wherein the medical device is one or more of a lead, a guidewire, a dilator, and a balloon catheter inserted into a catheter through the seal and the elastic component includes silicone.

Example 13 is a method of sealing around a device inserted through a seal. The method including providing an elastic component having a proximal end, a distal end, and an elongated trough adjacent the distal end, the elastic component having a slit that intersects the elongated trough, and inserting the device through the elastic component from the proximal end to the distal end and through the slit in the elongated trough.

Example 14 is the method of Example 13, wherein inserting the device includes inserting the device through a hole in the proximal end of the elastic component, and inserting the device through an elongated inner cavity in the elastic component.

Example 15 is the method of any one of Examples 13 and 14. The method including forming a fluid seal around the device inserted through the seal via one or more flaps of the elongated trough.

Example 16 is a seal configured to permit passage of a device through the seal. The seal including an elastic component having a proximal end, a distal end, and an elongated trough adjacent the distal end, wherein the elastic component has a slit that intersects the elongated trough.

Example 17 is the seal of Example 16, wherein the elastic component has an elongated inner cavity between the proximal end and the distal end, and the elongated inner cavity is parallel to the elongated trough.

Example 18 is the seal of Example 16, wherein the slit intersects the elongated trough at an oblique angle.

Example 19 is the seal of Example 16, wherein the slit intersects the elongated trough perpendicular to the elongated trough.

Example 20 is the seal of Example 16, wherein the elastic component includes one or more flaps of elastic material at the distal end and bottom of the elongated trough, the one or more flaps configured for forming a fluid seal around the device inserted through the seal.

Example 21 is the seal of Example 20, wherein the one or more flaps have a thickness in a range from 0.005 to 0.01 inches thick.

Example 22 is the seal of Example 16, wherein the elastic component has an opening at the proximal end for inserting the device through the elongated trough.

Example 23 is the seal of Example 16, wherein the elastic component has a longitudinal axis from the proximal end to the distal end and the longitudinal axis intersects the elongated trough.

Example 24 is the seal of Example 23, wherein the elastic component has an opening at the proximal end aligned with the longitudinal axis for inserting the device through the elongated trough.

Example 25 is the seal of Example 16, wherein a top profile of the elastic component is substantially one of circular, oblong, rectangular, and polygon shaped.

Example 26 is a seal configured to permit passage of a medical device through the seal. The seal including an elastic component having a proximal end, a distal end, and an elongated inner cavity having a depth extending between the proximal end and the distal end, the elongated inner cavity having an elongated trough adjacent the distal end and a slit that intersects the elongated trough.

Example 27 is the seal of Example 26, wherein the slit intersects the elongated trough at an oblique angle.

Example 28 is the seal of Example 26, wherein the slit intersects the elongated trough perpendicular to the elongated trough.

Example 29 is the seal of Example 26, wherein the elastic component includes one or more flaps of elastic material at the distal end and bottom of the elongated trough, the one or more flaps configured to form a fluid seal around the medical device to reduce leakage of blood and air through the seal.

Example 30 is the seal of Example 26, wherein the elastic component is configured to be cut along at least one side of the slit to remove the seal from the device.

Example 31 is the seal of Example 26, wherein the medical device is one or more of a lead, a guidewire, a dilator, and a balloon catheter inserted into a catheter through the seal and the elastic component includes silicone.

Example 32 is a method of sealing around a device inserted through a seal. The method including providing an elastic component having a proximal end, a distal end, an elongated trough adjacent the distal end, and a slit that intersects the elongated trough, and inserting the device through the elastic component from the proximal end to the distal end and through the slit in the elongated trough.

Example 33 is the method of Example 32, wherein inserting the device includes inserting the device through a hole in the proximal end of the elastic component, and inserting the device through an elongated inner cavity in the elastic component, the elongated inner cavity extending between the proximal end and the distal end.

Example 34 is the method of Example 32, including forming a fluid seal around the device inserted through the seal via one or more flaps of the elongated trough.

Example 35 is the method of Example 32, including removing the elastic component from the device by cutting the elastic component at the slit in the elastic component to a perimeter of the elastic component.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1:
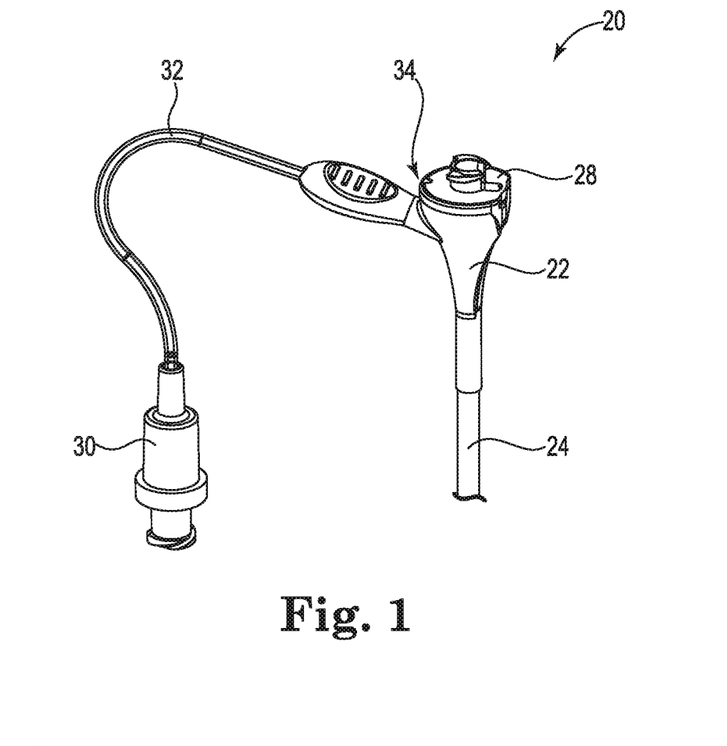
FIG. 1 is a diagram illustrating a lead delivery catheter, according to embodiments of the disclosure.

FIG. 1 is a diagram illustrating a lead delivery catheter 20, according to embodiments of the disclosure. The lead delivery catheter 20 is configured to be inserted into vasculature of a patient and advanced to a location in the body of the patient for diagnosis and/or treatment. In some embodiments, the lead delivery catheter 20 is configured to be inserted into the vasculature of the patient and advanced to the surface of the patient's heart. In some embodiments, the lead delivery catheter 20 is configured to guide a cardiac lead to the surface of the patient's heart.

Figure 2:
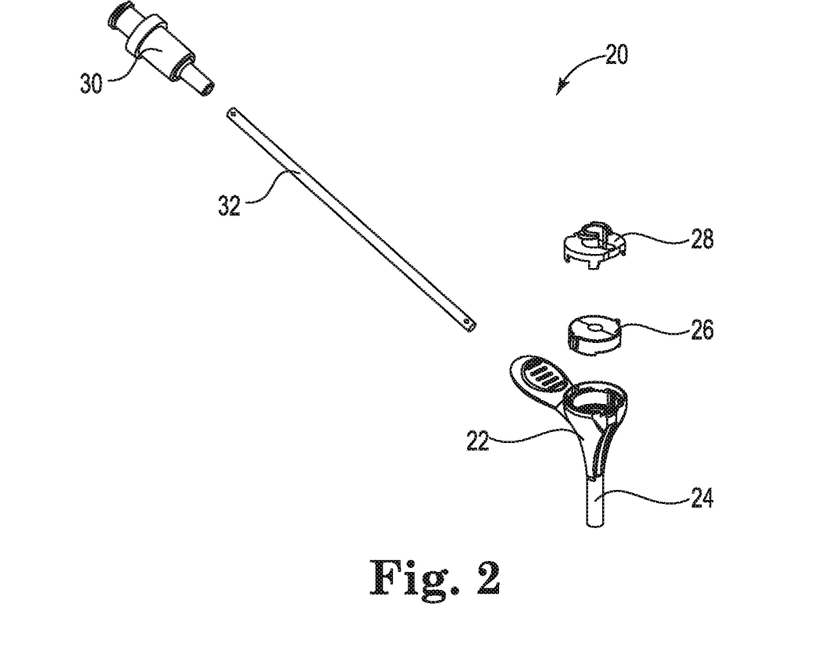
FIG. 2 is a diagram illustrating an exploded view of the lead delivery catheter of FIG. 1, according to embodiments of the disclosure.

FIG. 2 is a diagram illustrating an exploded view of the lead delivery catheter 20 of FIG. 1, according to embodiments of the disclosure. The lead delivery catheter 20 includes a housing 22 attached to a catheter 24 that is configured to be inserted into the patient's vasculature and advanced into the patient's body to the location in the body of the patient for diagnosis and/or treatment. The lead delivery catheter 20 includes a seal 26, a housing cap 28, a flush port 30, and tubing 32. The seal 26 is situated in the housing 22 and the housing cap 28 is attached to the housing 22. The seal 26 fits snugly inside the housing 22 to prevent fluids, such as air and liquids, from passing to and from the catheter 24 through or around the seal 26. The flush port 30 is attached to the housing 22 by the tubing 32. The flush port 30 can be used by medical personnel for attaching an empty syringe for the purpose of drawing a vacuum and thereby aspirating air that may be present from the inside of the catheter. The housing cap 28 can incorporate a luer for the attachment of a syringe and this orifice may be used to pass liquids, such as for flushing the catheter 24 and/or providing medications and fluids through the catheter 24 to the location in the body of the patient. In some embodiments, attaching the housing cap 28 to the housing 22 secures the seal 26 in the housing 22.

In operation, a catheter lead or other device is inserted through the seal 26 in the lead delivery catheter 20 to the location in the body of the patient. The seal 26 forms a fluid seal around the catheter lead or other device inserted through the seal 26 and reduces or prevents fluids from leaking through the seal 26 and past the catheter lead or other device. The seal 26 is configured to conform closely to various sized catheter leads and other devices placed through the seal 26 during the lead placement procedure. The seal 26 reduces or prevents blood from leaking out of and air being aspirated into the proximal end 34 of the lead delivery catheter 20.

FIGS. 3-7 are diagrams illustrating the seal 26, according to embodiments of the disclosure. The seal 26 permits passage of a device (not shown) through the seal 26 and the seal 26 forms a fluid seal around the device inserted through the seal 26. The fluid seal reduces or prevent fluids from flowing past the device and through the seal 26. In some embodiments, the device is a medical device. In some embodiments, the device is a catheter lead inserted into a catheter lumen through the seal 26. In some embodiments, the device is a medical device such as one or more of a catheter lead, a guidewire, a dilator, and a balloon catheter inserted into a catheter lumen through the seal 26. In some embodiments, the fluid seal reduces or prevent fluids, such as blood and/or air, from flowing past the device and through the seal 26.

Figure 3:
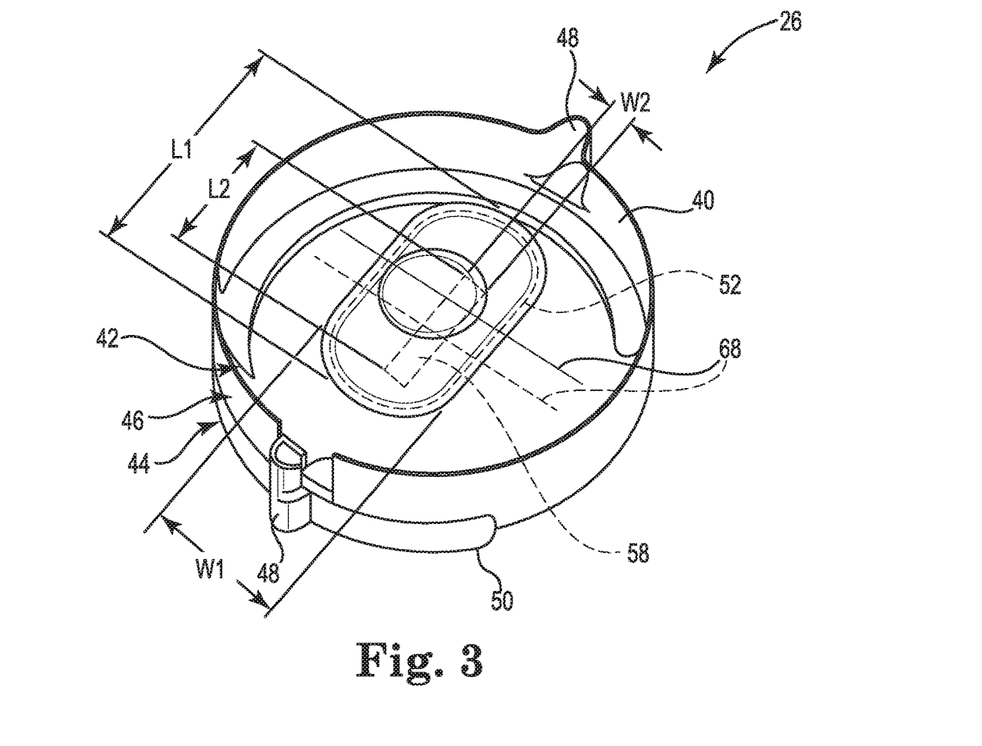
FIG. 3 is a diagram illustrating a top perspective view of the seal, according to embodiments of the disclosure.
Figure 4:
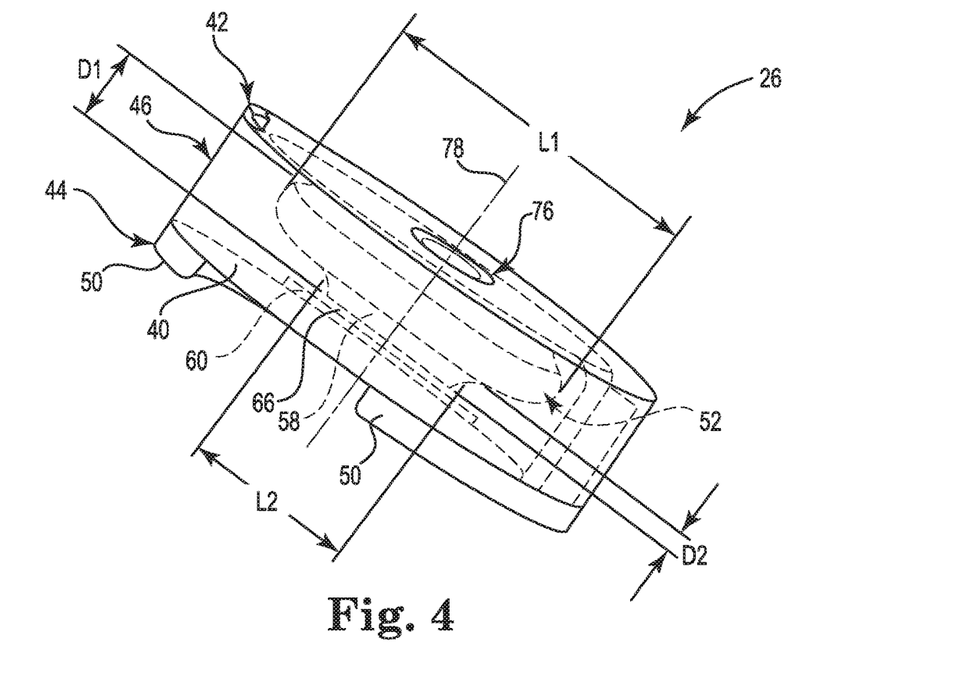
FIG. 4 is a diagram illustrating a side perspective view of the seal, according to embodiments of the disclosure.

FIGS. 3 and 4 are diagrams illustrating perspective views of the seal 26. FIG. 3 is a diagram illustrating a top perspective view of the seal 26, according to embodiments of the disclosure, and FIG. 4 is a diagram illustrating a side perspective view of the seal 26, according to embodiments of the disclosure.

Figure 5:
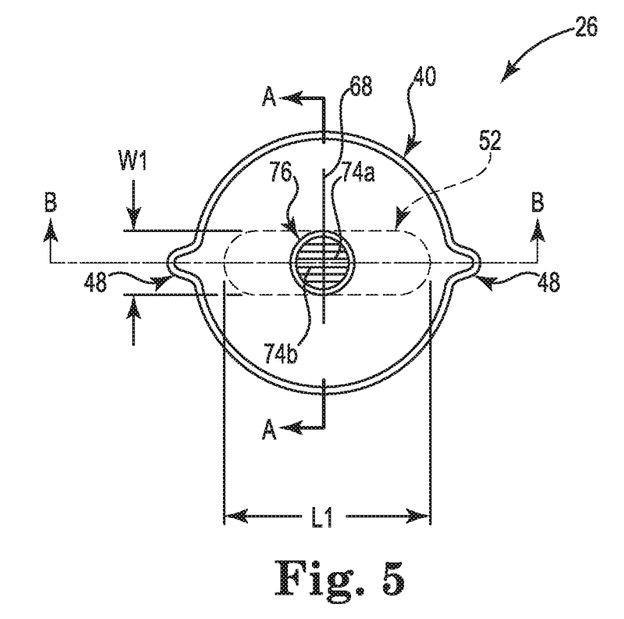
FIG. 5 is a diagram illustrating a top view of the seal, according to embodiments of the disclosure.
Figure 6:
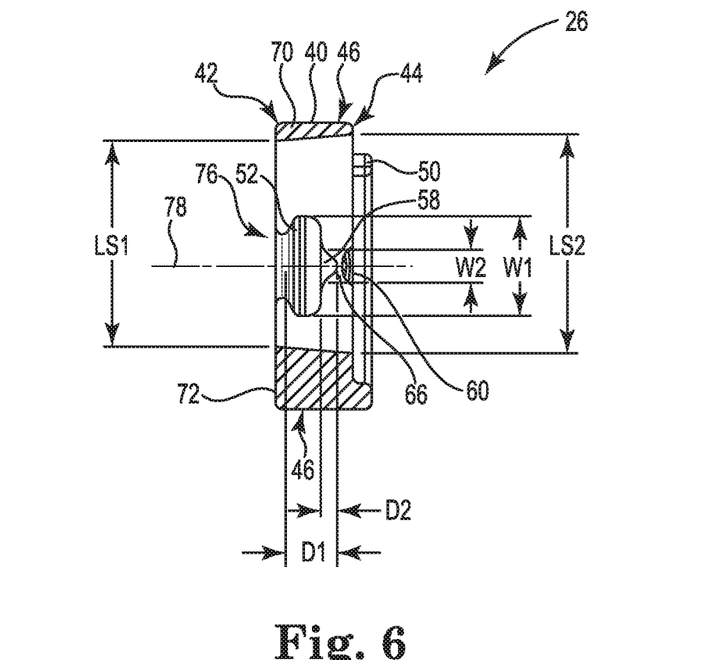
FIG. 6 is a diagram illustrating a cross-sectional view along the line A-A in FIG. 5, according to embodiments of the disclosure.
Figure 7:
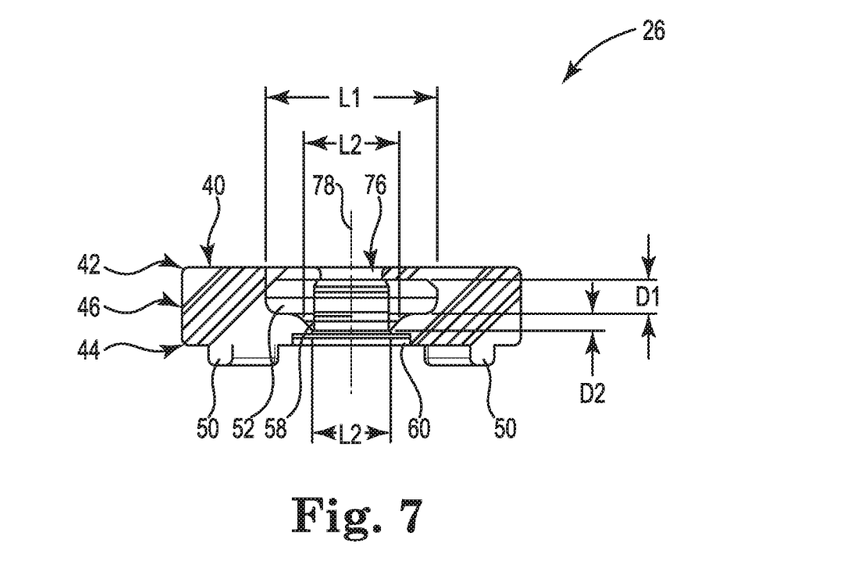
FIG. 7 is a diagram illustrating a cross-sectional view along the line B-B in FIG. 5, according to embodiments of the disclosure.

FIGS. 5-7 are diagrams illustrating top and cross-sectional views of the seal 26. FIG. 5 is a diagram illustrating a top view of the seal 26, according to embodiments of the disclosure. FIG. 6 is a diagram illustrating a cross-sectional view along the line A-A in FIG. 5, according to embodiments of the disclosure. FIG. 7 is a diagram illustrating a cross-sectional view along the line B-B in FIG. 5, according to embodiments of the disclosure.

The seal 26 is elastic or flexible and includes an elastic component 40. In some embodiments, material is injected into a mold and the molded elastic material is removed from the mold to form the seal 26. In some embodiments, the elastic component 40 includes silicone. In some embodiments, the elastic component 40 includes LIM 6030 material. In some embodiments, the elastic component 40 includes Dow 4720 material, which is tear resistant and has a low durometer such that it is very flexible and conforms well to devices inserted through it.

The elastic component 40 has a top profile, shown in FIG. 5, which is substantially circular. In other embodiments, the elastic component 40 can be a different shape. For example, in some embodiments, the elastic component 40 has a top profile that is oblong. In some embodiments, the elastic component 40 has a top profile that is rectangular. In some embodiments, the elastic component 40 has a top profile that is polygon shaped.

The elastic component 40 has a proximal end 42, a distal end 44, and sides 46 extending between the proximal end 42 and the distal end 44. Also, the elastic component 40 includes placement nubs 48 that are used as keys for situating the seal 26 in the housing 22. In some embodiments, the placement nubs 48 are situated on opposing sides 46 of the elastic component 40. In some embodiments, the placement nubs 48 extend from the proximal end 42 to the distal end 44 of the elastic component 40. Also, in some embodiments, the elastic component 40 includes a placement hub/seal 50 at the distal end 44 of the elastic component 40. The placement hub/seal 50 can be used to situate the seal 26 in the housing and/or to provide a fluid seal with the housing 22.

The elastic component 40 has an elongated inner cavity 52 between the proximal end 42 and the distal end 44. The elongated inner cavity 52 has a length L1, a width W1, and a depth D1 that extends between the proximal end 42 and the distal end 44 of the elastic component 40. The length L1 of the elongated inner cavity 52 is greater than the width W1 of the elongated inner cavity 52 and the length L1 extends between the sides 46 of the elastic component 40.

Toward the distal end 44, the elongated inner cavity 52 has a first elongated trough 58 that has a trough length L2, a trough width W2, and a trough depth D2. The trough length L2 and the trough width W2 are parallel to the length L1 and width W1 of the elongated inner cavity 52, respectively. The elongated trough 58 is adjacent the distal end 44 of the elastic component 40 and has a bottom 66 at the distal end 44. In some embodiments, the elastic component 40 has a second elongated trough 60 at the distal end 44 of the elastic component 40 and opposing the first elongated trough 58, with the bottom 66 of the elongated trough 58 between the first elongated trough 58 and the second elongated trough 60. In some embodiments, the second elongated trough 60 includes a length and a width that are parallel to and/or collinear with the length L2 and width W2 of the first elongated trough 58.

In some embodiments, the elastic component 40 includes the first elongated trough 58 that has the trough length L2, the trough width W2, and the trough depth D2, but the elastic component 40 does not include the elongated inner cavity 52 between the proximal end 42 and the distal end 44 of the elastic component 40. In these embodiments, the elongated trough 58 is adjacent the distal end 44 of the elastic component 40 and has a bottom 66 at the distal end 44. Also, in some of these embodiments, the elastic component 40 has the second elongated trough 60 at the distal end 44 of the elastic component 40 and opposing the first elongated trough 58, with the bottom 66 of the elongated trough 58 between the first elongated trough 58 and the second elongated trough 60. In some embodiments, the second elongated trough 60 includes a length and a width that are parallel to and/or collinear with the length L2 and width W2 of the first elongated trough 58.

The elastic component 40 has a slit 68 cut into it that intersects the elongated inner cavity 52, including the elongated trough 58. In embodiments that include the elongated trough 58, but not the elongated inner cavity 52, the slit 68 intersects the elongated trough 58. The slit 68 extends from the proximal end 42 to the distal end 44 of the elastic component 40, and the slit 68 extends through the bottom 66 of the elongated trough 58. In some embodiments, the slit 68 intersects the elongated trough 58 perpendicular to the trough length L2 of the elongated trough 58. In some embodiments, the slit 68 intersects the trough length L2 of the elongated trough 58 at an oblique angle. In some embodiments, the elastic component 40 has multiple slits cut into it that intersect the elongated trough 58, such that multiple devices may be inserted through the elastic component 40 and the multiple slits in the elongated trough 58.

The slit 68 has a first length LS1 (as shown in FIG. 6) at the proximal end 42 and a second length LS2 at the distal end 44. The slit 68 does not extend from one side 46 of the elastic component 40 to the other side 46 of the elastic component 40. Instead, a first portion 70 of the elastic component 40 is left at one side of the slit 68 and a second portion 72 of the elastic component 40 is left at the other side of the slit 68. In use, one or both portions 70 and 72 can be cut to separate the elastic component 40 and remove it from the device inserted through the seal 26. In some embodiments, the slit 68 is coated with oil to keep the slit 68 from sealing itself and/or to maintain the slit 68. In some embodiments, the slit 68 is coated with a silicone oil to keep the slit 68 from sealing itself and/or to maintain the slit 68.

In some embodiments, the slit 68 extends all the way through one side of the elastic component 40 such that the slit 68 does not need to be cut further to remove the seal. In some embodiments, the slit 68 extends all the way through both opposing sides of the elastic component 40, to form two separate parts, such that the slit 68 does not need to be cut further to remove the seal. In both of these situations, a hub or similar restraining device may be used to hold the seal together.

The slit 68 intersects the trough length L2 of the elongated trough 58 to cut the lengthwise sides of the elongated trough 58 and the bottom 66 of the elongated trough 58 between the lengthwise sides of the elongated trough 58. The slit 68 cuts both the thin bottom 66 and the thicker, firmer lengthwise sides of the elongated trough 58. The bottom 66 of the elongated trough 58 is cut by the slit 68 to form one or more bottom flaps 74a and 74b (shown in FIG. 5) of material at the bottom 66 of the elongated trough 58 and the distal end 44 of the elastic component 40. The one or more flaps 74a and 74b are thin flaps of material between the thicker, firmer sides of the elongated trough 58. The one or more flaps 74a and 74b are configured to apply a lighter pressure or force on the inserted device and stretch around an inserted device. The flaps 74a and 74b seal around the inserted device to close the openings on opposing sides of the inserted device along the length of the slit 68. Openings that otherwise present a cat's eye shape with the inserted device, where leakage can occur at the openings. The thicker, firmer lengthwise sides of the elongated trough 58 act as a bulk spring force to compress the openings of the cat's eye closed or shut and assist the flaps 74a and 74b in sealing against the inserted device. Thus, the elongated trough 58 including the sides of the elongated trough 58 and the one or more flaps 74a and 74b form a fluid seal around the device inserted through the seal 26. In some embodiments, the one or more flaps 74a and 74b have a thickness in a range from 0.005 to 0.01 inches thick. In some embodiments, the one or more flaps 74a and 74b have a thickness of 0.009 inches thick. In some embodiments, the slit 68 is coated with oil to assist in closing the openings formed by the device inserted through the slit 68. In some embodiments, the slit 68 is coated with a silicone oil to assist in closing the openings formed by the device inserted through the slit 68.

The elastic component 40 has a longitudinal axis 78 from the proximal end 42 to the distal end 44. In some embodiments, the longitudinal axis 78 intersects the elongated inner cavity 52 and the elongated trough 58. In some embodiments, the elastic component 40 has an opening 76 at the proximal end 42 that opens into the elongated inner cavity 52. In some embodiments, the opening 76 is at the longitudinal axis 78 and the opening 76 opens into the elongated inner cavity 52. In some embodiments, the opening 76 functions as a target for inserting the device through the elastic component 40, including through the elongated inner cavity 52 and the slit 68 at the bottom 66 of the elongated trough 58.

In operation of embodiments, the device is inserted through the opening 76, the elongated inner cavity 52, and the slit 68 at the bottom 66 of the elongated trough 58. The one or more flaps 74a and 74b apply a lighter pressure or force on the inserted device to stretch around the inserted device and the thicker, firmer sides of the elongated trough 58 act as a spring force to assist the flaps 74a and 74b in sealing against the inserted device. The sides of the elongated trough 58 and the one or more flaps 74a and 74b form a fluid seal around the device inserted through the seal 26.

Figure 8:
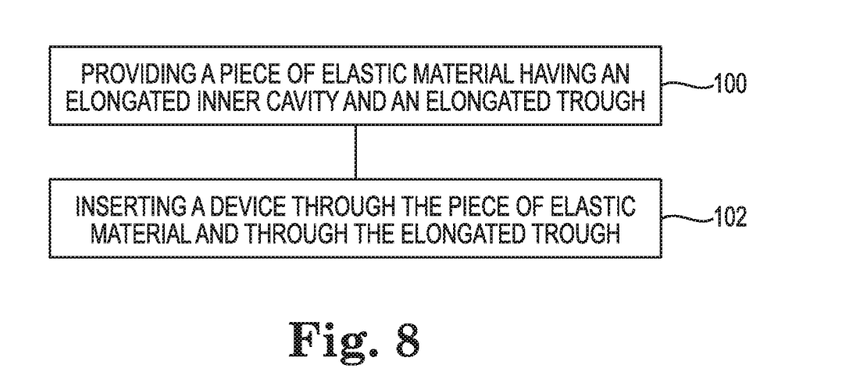
FIG. 8 is a flow chart diagram illustrating a method of sealing around a device inserted through a seal, according to embodiments of the disclosure.

FIG. 8 is a flow chart diagram illustrating a method of sealing around a device inserted through a seal, according to embodiments of the disclosure.

The method, at 100, includes providing an elastic component having a proximal end, a distal end, and an elongated inner cavity situated between the proximal end and the distal end of the elastic component. The elongated inner cavity has a depth that extends between the proximal end and the distal end of the elastic component, and the elongated inner cavity has a length and a width that extend between sides of the elastic component. Also, the elongated inner cavity has an elongated trough adjacent the distal end of the elastic component and parallel with the elongated inner cavity. In other embodiments, the elastic component has the elongated trough adjacent the distal end of the elastic component, but not the elongated inner cavity.

At 102, the method includes inserting a device through the elastic component from the proximal end to the distal end and through the elongated trough. In some embodiments, inserting the device includes inserting the device through a hole at the proximal end of the elastic component. In some embodiments, inserting the device includes inserting the device through a slit in the elongated trough. In some embodiments, the elongated trough has a bottom at the distal end of the elastic component with a slit in it such that a fluid seal is formed around the device with one or more flaps at the bottom of the elongated trough.

In some embodiments, the method further includes removing the elastic component by cutting the elastic component at the slit in the elastic component to a perimeter or side of the elastic component. This would be done after a device, such as a catheter, has served its purpose in conveying a lead to a target location. The seal would be cut and the entire catheter and the seal would be removed and discarded.

Figure 9:
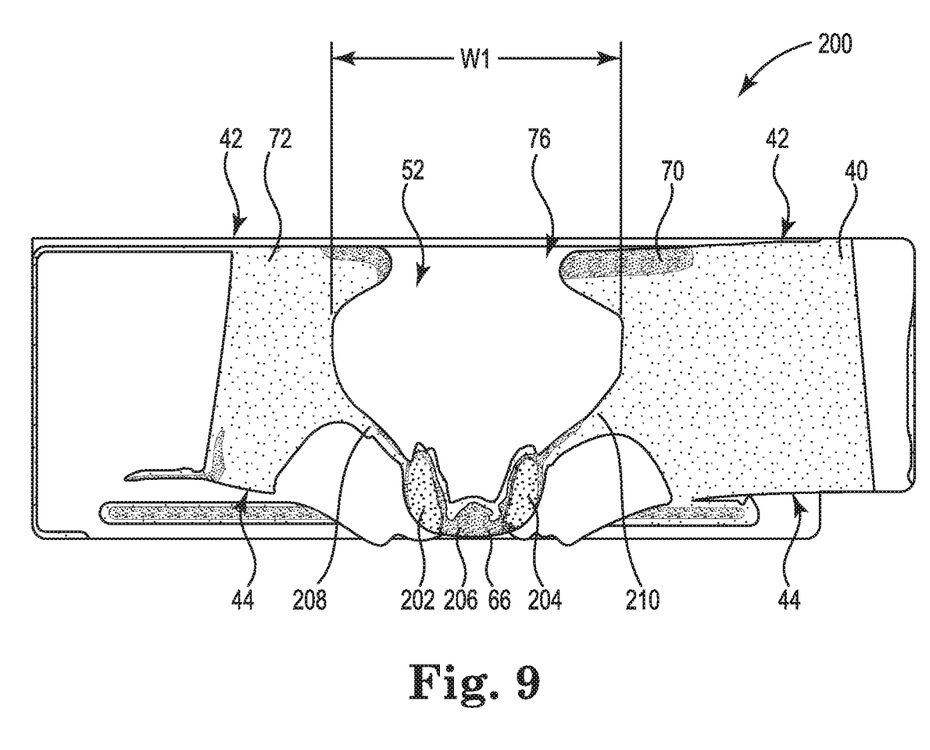
FIG. 9 is a diagram illustrating a finite element analysis of the seal with a device inserted through the seal, according to embodiments of the disclosure.

FIG. 9 is a diagram illustrating a finite element analysis 200 of the seal 26 with a device inserted through the seal 26, according to embodiments of the disclosure. The finite element analysis 200 was performed at the slit 68, along the line A-A in FIG. 5. A simulated device (not shown) was inserted through the seal 26 and the force applied by the seal 26 on the device was mapped to determine the efficacy of the seal 26. The simulated device can be any suitable device, such as a mandrel, a medical device, or a catheter lead.

The finite element analysis 200 includes the opening 76 at the proximal end 42 of the elastic component 40 and the elongated inner cavity 52 situated between the proximal end 42 and the distal end 44 of the elastic component 40. The width W1 of the elongated inner cavity 52 lies horizontally in the plane of the diagram and the length L1 of the elongated inner cavity 52 extends into and out of the plane of the diagram. The first portion 70 of the elastic component 40 is at one side of the finite element analysis 200 and the second portion 72 of the elastic component 40 is at the other side of the finite element analysis 200.

The device is inserted through the opening 76 and elongated inner cavity 52 and through the slit 68 in the bottom 66 of the elongated trough 58. The finite element analysis 200 shows that the sides of the elongated trough 58 apply a great deal of force at 202 and 204 to the device and the bottom 66 of the elongated trough 58 applies a much lesser force at 206, where the one or more flaps 74a and 74b stretch around the inserted device to make contact with the device. In addition, the finite element analysis 200 shows that the sides of the elongated inner cavity 52 at portions 70 and 72 and extending to the sides of the elongated trough 58 provide a fluid seal at 208 and 210 around the device to prevent fluid from leaking through the seal 26.

The one or more flaps 74a and 74b at the bottom 66 apply a light force at 206 to the inserted device and stretch around the inserted device such that the sides of the elongated trough 58 and extending to the elongated inner cavity 52 form a fluid seal at 202, 204, 208, and 210 completely around the inserted device. Substantially no gap that has been seen in previous seal configurations is left between the device and the seal 26 along the slit 68.

Figure 10:
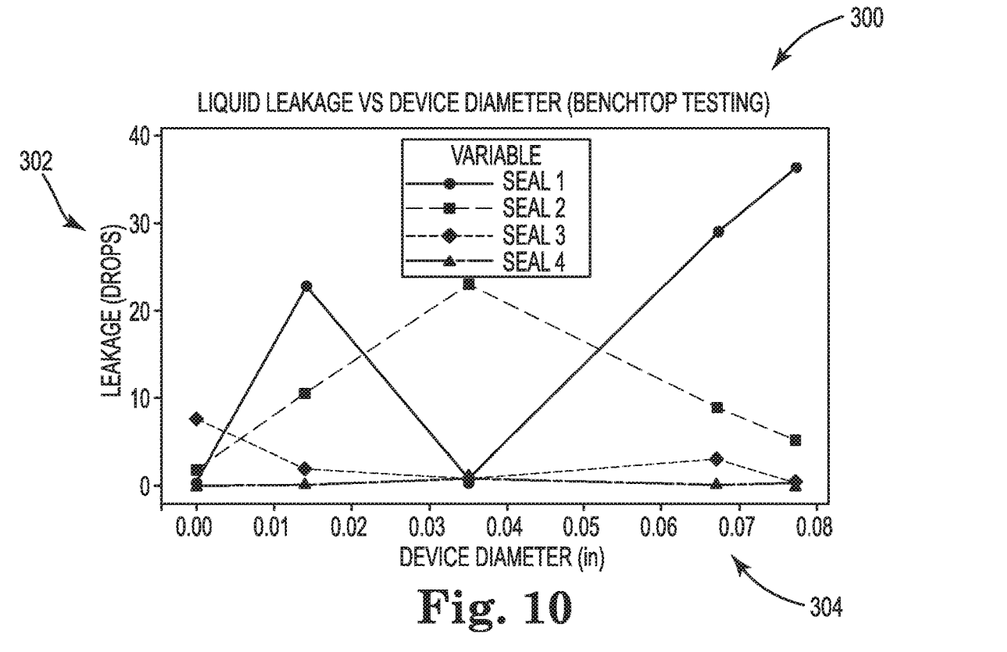
FIG. 10 is a diagram illustrating a graph of liquid leakage through various seals versus different device diameters.

FIG. 10 is a diagram illustrating a graph 300 of liquid leakage through various seals versus different inserted device diameters. Liquid leakage in drops is graphed on the y-axis at 302 versus inserted device diameter in inches on the x-axis at 304. Each of seal 1 and seal 2 is a previous seal configuration, which does not include the features of seal 26. Seal 3 is similar to seal 26 described above and made out of a material named LIM 6030 and seal 4 is similar to seal 26 described above and made out of a material named Dow 4720.

Liquid leakage through each of the previous seal configurations of seal 1 and seal 2 varies a great deal more than the liquid leakage through each of seal 3 and seal 4. Also, the liquid leakage through each of the previous seal configurations of seal 1 and seal 2 is greater than the liquid leakage through each of seal 3 and seal 4.

Liquid leakage through seal 1 varies from about 30 drops at a device diameter between 0.01 and 0.02 inches, to a low approaching 0 drops at a device diameter between 0.03 and 0.04 inches, to about 30 drops at a device diameter between 0.06 and 0.07 inches, and to a high of about 40 drops at a device diameter between 0.07 and 0.08 inches. Also, liquid leakage through seal 2 varies from about 10 drops at a device diameter between 0.01 and 0.02 inches, to about 20 drops at a device diameter between 0.03 and 0.04 inches, to about 10 drops at a device diameter between 0.06 and 0.07 inches, and to about 5 drops at a device diameter between 0.07 and 0.08 inches.

In contrast, the liquid leakage through seal 3 varies very little, from about 3 drops at a device diameter between 0.01 and 0.02 inches, to a low approaching 0 drops at a device diameter between 0.03 and 0.04 inches, to about 6 drops at a device diameter between 0.06 and 0.07 inches, and back to a low approaching 0 drops at a device diameter between 0.07 and 0.08 inches. Similarly, the liquid leakage through seal 4 varies very little, from a low of about 0 drops at a device diameter between 0.01 and 0.02 inches and at a device diameter between 0.03 and 0.04 inches, to about 4 drops at a device diameter between 0.06 and 0.07 inches, and back to a low approaching 0 drops at a device diameter between 0.07 and 0.08 inches.

From the above, each of seal 3 and seal 4, which are similar to seal 26, provide a better liquid seal than the previous seal configurations of seal 1 and seal 2.

Figure 11:
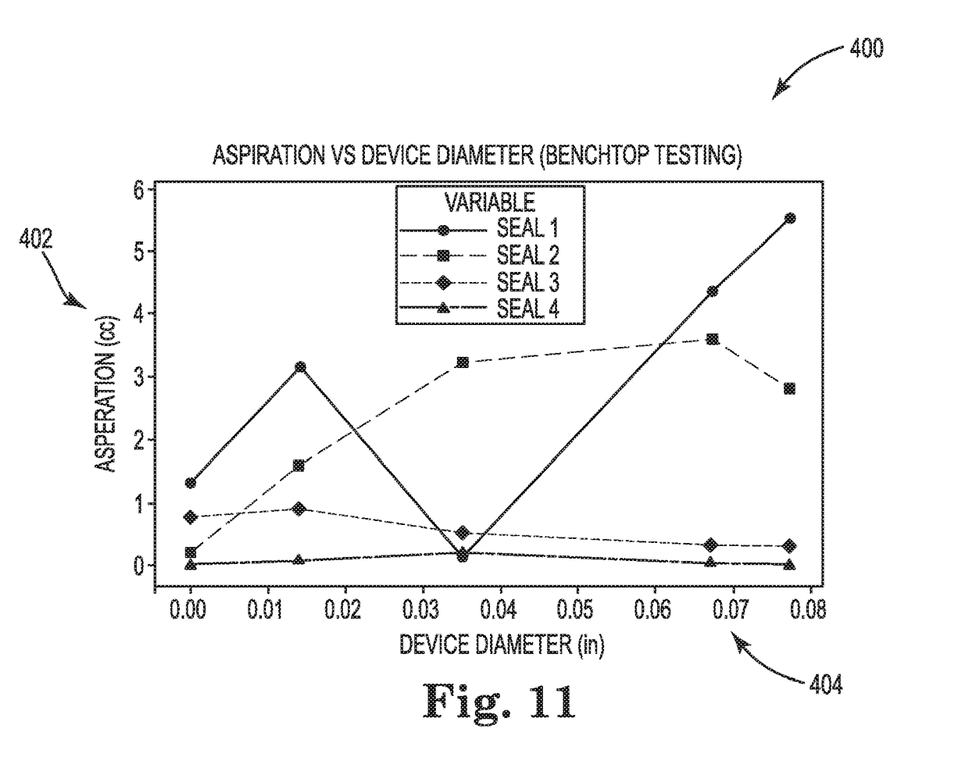
FIG. 11 is a diagram illustrating a graph of aspiration, such as air aspiration, through various seals versus different device diameters.

FIG. 11 is a diagram illustrating a graph 400 of aspiration, such as air aspiration, through various seals versus different inserted device diameters. Aspiration in cubic centimeters (cc) is graphed on the y-axis at 402 versus inserted device diameter in inches on the x-axis at 404. Each of seal 1 and seal 2 is a previous seal configuration, which does not include the features of seal 26. Seal 3 is similar to seal 26 and made out of a material named LIM 6030 and seal 4 is similar to seal 26 and made out of a material named Dow 4720.

Aspiration through each of the previous seal configurations of seal 1 and seal 2 varies a great deal more than aspiration through each of seal 3 and seal 4. Also, the aspiration through each of the previous seal configurations of seal 1 and seal 2 is greater than the aspiration through each of seal 3 and seal 4.

Aspiration through seal 1 varies from about 3.3 cc at a device diameter between 0.01 and 0.02 inches, to a low approaching 0 cc at a device diameter between 0.03 and 0.04 inches, to about 4.0 cc at a device diameter between 0.06 and 0.07 inches, and to a high of about 4.8 cc at a device diameter between 0.07 and 0.08 inches. Also, aspiration through seal 2 varies from about 3.3 cc at a device diameter between 0.01 and 0.02 inches, to about 3.0 cc at a device diameter between 0.03 and 0.04 inches, to about 3.6 cc at a device diameter between 0.06 and 0.07 inches, and to about 2.8 cc at a device diameter between 0.07 and 0.08 inches.

It is interesting to note that in some situations an aspiration volume of 3.0 cc is a worrisome amount of air and that an aspiration volume of 4.0 cc would lead to rejecting the device and disposing of the catheter and lead, at an expense of thousands of U.S. dollars and a procedural delay. The reason for this is that there would be no way of telling whether the air aspirated through the seal or from elsewhere in the device and, to play it safe, the latter would have to be assumed.

In contrast, the aspiration through seal 3 varies very little, from about 1 cc at a device diameter between 0.01 and 0.02 inches, to a low approaching 0 cc at a device diameter between 0.03 and 0.04 inches, to about 1 cc at a device diameter between 0.06 and 0.07 inches, and back to a low approaching 0 cc at a device diameter between 0.07 and 0.08 inches. Similarly, the aspiration through seal 4 varies very little, from about 0.2 cc at a device diameter between 0.01 and 0.02 inches and at a device diameter between 0.03 and 0.04 inches and at a device diameter between 0.06 and 0.07 inches, to a low approaching 0 cc at a device diameter between 0.07 and 0.08 inches.

From the above, each of seal 3 and seal 4, which are similar to seal 26, provide a better aspiration seal than the previous seal configurations of seal 1 and seal 2.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A seal configured to permit passage of a device through the seal, the seal comprising:
    an elastic component having a proximal end and a distal end, the elastic component including:
        an elongated trough having a generally rectangular profile with a first length and a first width that is less than the first length, the elongated trough situated adjacent the distal end,
        wherein the elastic component has a slit that intersects the elongated trough and includes one or more flaps of elastic material at the distal end and bottom of the elongated trough, the one or more flaps configured for forming a fluid seal around the device inserted through the seal.

2. The seal of claim 1, wherein the elastic component has an elongated inner cavity having a second length and a second width that is less than the second length, the elongated inner cavity situated between the proximal end and the elongated trough, wherein the first length of the elongated trough is parallel to the second length of the elongated inner cavity.

3. The seal of claim 1, wherein the slit intersects the elongated trough at an oblique angle.

4. The seal of claim 1, wherein the slit intersects the elongated trough perpendicular to the elongated trough.

5. The seal of claim 1, wherein the one or more flaps have a thickness in a range from 0.005 to 0.01 inches thick.

6. The seal of claim 1, wherein the elastic component has an opening at the proximal end for inserting the device through the elongated trough.

7. The seal of claim 1, wherein the elastic component has a longitudinal axis from the proximal end to the distal end and the longitudinal axis intersects the elongated trough.

8. The seal of claim 7, wherein the elastic component has an opening at the proximal end aligned with the longitudinal axis for inserting the device through the elongated trough.

9. The seal of claim 1, wherein a top profile of the elastic component is substantially one of circular, oblong, rectangular, and polygon shaped.

10. A seal configured to permit passage of a medical device through the seal, the seal comprising:
    an elastic component having a proximal end, a distal end, and an elongated inner cavity having a depth extending between the proximal end and the distal end, the elongated inner cavity having a first length and a first width that is less than the first length and an elongated trough having a second length and a second width that is less than the second length, the elongated trough situated adjacent the distal end, wherein the first length of the elongated inner cavity is parallel to the second length of the elongated trough and the elastic component has a slit that intersects the elongated trough, wherein the elastic component includes one or more flaps of elastic material at the distal end and bottom of the elongated trough, the one or more flaps configured to form a fluid seal around the medical device to reduce leakage of blood and air through the seal.

11. The seal of claim 10, wherein the slit intersects the elongated trough at an oblique angle.

12. The seal of claim 10, wherein the slit intersects the elongated trough perpendicular to the elongated trough.

13. The seal of claim 10, wherein the elastic component is configured to be cut along at least one side of the slit to remove the seal from the device.

14. The seal of claim 10, wherein the medical device is one or more of a lead, a guidewire, a dilator, and a balloon catheter inserted into a catheter through the seal and the elastic component includes silicone.

15. A method of sealing around a device inserted through a seal, comprising:
    providing an elastic component having a proximal end, a distal end, an elongated trough having a generally rectangular profile with a first length and a first width that is less than the first length, the elongated trough situated adjacent the distal end, and a slit that intersects the elongated trough;
    inserting the device through the elastic component from the proximal end to the distal end and through the slit in the elongated trough; and
    forming a fluid seal around the device inserted through the seal via one or more flaps of the elongated trough.

16. The method of claim 15, wherein inserting the device comprises:
    inserting the device through a hole in the proximal end of the elastic component; and
    inserting the device through an elongated inner cavity in the elastic component, the elongated inner cavity extending between the proximal end and the distal end.

17. The method of claim 15, comprising:
    removing the elastic component from the device by cutting the elastic component at the slit in the elastic component to a perimeter of the elastic component.

* * * * *